(12) United States Patent
Kling

(10) Patent No.: US 6,217,692 B1
(45) Date of Patent: Apr. 17, 2001

(54) ELASTIC LAMINATE FOR AN ABSORBING ARTICLE, AND A METHOD OF PRODUCING THE ELASTIC LAMINATE

(75) Inventor: Robert Kling, Skene (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/194,587

(22) PCT Filed: May 26, 1997

(86) PCT No.: PCT/SE97/00857

§ 371 Date: Nov. 30, 1998

§ 102(e) Date: Nov. 30, 1998

(87) PCT Pub. No.: WO97/45261

PCT Pub. Date: Dec. 4, 1997

(30) Foreign Application Priority Data

May 31, 1996 (SE) .................................................... 9602131

(51) Int. Cl.[7] .................................................... B32B 31/00
(52) U.S. Cl. .................... 156/229; 156/161; 156/269; 428/77; 604/385.24
(58) Field of Search ................... 156/229, 164, 156/163, 161, 264, 269, 358; 428/77, 78; 604/385.24, 386, 387

(56) References Cited

U.S. PATENT DOCUMENTS

| | | | | |
|---|---|---|---|---|
| 4,911,701 | * | 3/1990 | Mavinkurve | 604/385.2 |
| 4,915,767 | * | 4/1990 | Rajala et al. | 156/440 |
| 5,234,422 | * | 8/1993 | Sneller et al. | 604/385.2 |
| 5,558,663 | * | 9/1996 | Weinberger et al. | 604/387 |
| 5,567,260 | * | 10/1996 | McFall | 156/201 |
| 5,714,027 | * | 2/1998 | Taub | 156/204 |
| 5,779,691 | * | 7/1998 | Schmitt | 604/386 |
| 5,964,973 | * | 10/1999 | Heath et al. | 156/161 |

FOREIGN PATENT DOCUMENTS

| | | |
|---|---|---|
| 0 113 976 A2 | 7/1984 | (EP) . |
| 0 170 922 A1 | 2/1986 | (EP) . |
| WO80/00676 | 4/1980 | (WO) . |

* cited by examiner

*Primary Examiner*—Richard Crispino
*Assistant Examiner*—Sue A. Purvis
(74) *Attorney, Agent, or Firm*—Burns, Doane, Swecker & Mathis, L.L.P.

(57) ABSTRACT

The invention relates to a method of manufacturing an elastic laminate (1) in which a web (10) of elastic material is continuously fed out, stretched and attached in stretched condition to a supporting material in the shape of a moving support web (2). The support web (2) has a greater extension across the direction of movement of the web (2) than the web of elastic material (10), causing sections (18) of the supporting web (2) to protrude latitudinally on each side of the web (10) of elastic material. The laminate is divided into two longitudinal web-parts (20, 21) along a curved dividing line (15), causing the web (10) of elastic material to be cut off in a plurality of pieces (26) and tongues (23) of material formed from the divided web (10) of elastic material and flaps (25) laminated thereto from the supporting web (2) protrude out from, and are connected to, strip-formed edge-sections (18) of the supporting web (2) on both sides of the dividing line (15). The laminate can be used for forming elastic elements on absorbing articles such as diapers, incontinence protectors or sanitary napkins.

18 Claims, 5 Drawing Sheets

ELASTIC LAMINATE FOR AN ABSORBING ARTICLE, AND A METHOD OF PRODUCING THE ELASTIC LAMINATE

TECHNICAL FIELD

The invention relates to a method of producing an elastic laminate wherein an elastic web of material is continuously fed, stretched and attached in stretched condition to a support material in the form of a moving web of material. The invention also relates to an elastic laminate, and an absorbing article such as a diaper, an incontinence protector or a sanitary napkin comprising the elastic laminate.

BACKGROUND

In an absorbing article intended for the absorption of body fluids, it can be desirable for several reasons to attach one or several elastic elements to the article. Such elastic elements are, for example, used in order to form a tight-fitting edge around the leg- and waist openings of a diaper. Furthermore, elastic elements are used to form raised fluid leakage barriers along edge sections of diapers, incontinence protectors and sanitary napkins. It is also possible to use elastic elements to shape an absorbing article so that it conforms better to the body of a user, or so that the article obtains a shape suitable for reception of fluid.

Absorbing articles of the kind intended here are usually produced by continuously joining the different components to form a moving web of material. The simplest way of attaching elastic elements to the absorbing articles is to feed the elastic elements in the form of endless strips or threads and to attach them to the moving web of material. The elastic elements are attached to the web of material in stretched condition, and when the absorbing articles are cut or severed from the web of material, the stretching of the elastic elements ceases, causing them to contract, and at the same time, to contract the material of the absorbing article. Since it is extremely difficult to handle separate, three-dimensionally shaped articles in a manufacturing process, it is desirable to perform the cutting step at as late a stage in the process as possible.

A great disadvantage of attaching continuous elastic strips or threads to the absorbing articles is, however that it is impossible to control the application of the elastic elements to those sections of the articles where it is suitable to have elastic elements.

It is, for example, common during manufacturing of training pants or diapers of the so-called all-in-one type to provide the diaper with elastic elements arranged along the leg-edges in order to create tight-fitting elastic leg cuffs. The term all-in-one diapers refers to diapers which consist of an absorbing insert permanently attached to a liquid imperme- able outer cover and which may be joined together around the lower portion of the torso of a user in a pant-like way.

By way of example, elastic threads or strips are used as elastic elements, said threads or strips being attached in a stretched condition along the side-edges or the diaper. When the stretching of the elastic organs ceases the side-edges of the diaper contract. Apart from the fact that elastic leg cuffs are thus formed, those sections of the side-edges which, during use of the diaper, are intended to be in contact with the hips of the user are also wrinkled. Such wrinkling has a number of negative effects. For example the wrinkles of the diaper may cause pressure and be abrasive against the skin of the user. Furthermore, they reduce the fit of the diaper and reduce the possibility of concealing the diaper under the clothes. The presence of wrinkles and folds also makes it difficult to attach fastening means for fastening of the diaper during use.

Sanitary napkins and incontinence protectors for slightly incontinent persons belong to a category of absorbing articles which have a relatively small size. Such articles are intended to essentially fit in the crotch-area of a user and be applied over the genitals of the user, in order to immediately capture secreted body liquid. Absorbing articles of this kind are usually supported by being detachably attached, for example with self-adhesive glue, inside underwear.

It has become increasingly common to provide absorbing articles such as sanitary napkins and incontinence protectors with elastic elements which extend along the side-edges. The elastic elements serve a number of different purposes. By positioning the elastic elements at a distance from the absorption body of the article, it is for example possible to obtain raised fluid barriers along the side-edges. Furthermore, the elastic elements contract the side-edges of the article so that the article is curved in the longitudinal direction, which leads to the formation of a liquid-receiving bowl, at the same time as the curving brings the shape of the article into conformity with the shape of the users body.

As with the earlier discussed all-in-one diapers it may, however, be desirable to arrange elastic elements only along sections of the side-edges of the articles. Sanitary napkins and protectors for slightly incontinent persons are usually worn by healthy and active adults. It is thus extremely important that the articles have a discrete shape which permits them to be worn under ordinary clothing without being visible to others. For this reason, the end-sections of the article are kept free from elastic elements, whereby the end-sections can be in smooth contact with the body of the user so that conspicuous wrinkles and folds are avoided.

In order to solve the problem of attaching elastic elements only along certain sections of an absorbing article, it has been suggested to kill the elastic effect where it is not wanted, for example by heating or by chemical treatment of the elastic elements.

Another way of avoiding elastic effect within certain sections of an absorbing article is to only glue, or in some other way attach, those parts of the elastic element which are intended to be active in the article. Alternatively, when applying adhesive to the entire elastic elements, it is possible to treat those sections where no effect is wanted, with, for example, silicon spray so that they do not adhere to adjacent layers of material or other components. When cutting the elastic elements, these contract and leave a section of the article free from elastic elements in the vicinity of the cut. However, in so doing, an unnecessarily large amount of elastic material is used, and the manufacturing process is made more expensive and more difficult due to the necessity of synchronizing the treatment of the elastic elements with the cutting of the separate absorbing articles. The substances which are used to prevent the elastic organs from adhering can furthermore cause problems if they, by mistake happen to be applied in a wrong position in the process, since attachment of other components in the article may thus be made possible.

A number of various ways of handling and attaching discrete elastic pieces of material have also been suggested. Such solutions, are however complicated and costly and can not be used at the high speeds of manufacturing which are necessary nowadays in order to achieve profitable and rational manufacturing of disposable absorbing articles.

OBJECT OF THE INVENTION

It is thus an object of the invention to provide a method of continuously attaching discrete elastic elements to absorbing articles which are cut from a moving web of material.

A further object of the invention is to transport and attach discrete elastic organs to a moving web of material in a controlled manner.

It is a further object of the invention to achieve an efficient and material-saving method of attaching discrete elastic elements to absorbing articles.

CHARACTERISTICS OF THE INVENTION

The present invention solves the problems associated with handling discrete elastic elements in a manufacturing process by attaching the elastic web of material to a supporting web which has a larger extension across the direction of movement of the web than the web of elastic material, and by attaching the web of elastic material to the supporting web with sections of supporting web protruding laterally from each side of the web of elastic material, whereafter the laminate comprising the supporting web and the web of elastic material is split into two longitudinally extending web-sections along a curve-shaped dividing line which extends essentially in the direction of movement of the supporting web, inside the edges of the supporting web, and which moves back and forth across the web of elastic material, whereby tongues of material formed from section of the web of elastic material together with flaps of the supporting web which have been laminated to these protrude from and are connected to strip-shaped edge-sections of the supporting web on both sides of the dividing line.

In a preferred embodiment, the dividing line runs essentially along the longitudinal centre-line of the web of elastic material and curves out in both directions form the mid-line with an amplitude corresponding to at least half the width of the web of elastic material. It is thereby suitable if the web of elastic material is attached to the supporting web with the longitudinal centre-line of the web of elastic material generally coinciding with the longitudinal mid-line of the supporting material.

The laminate may preferably be divided into two symmetrical halves along the dividing line, with the protruding tongues of material on each half of the web having essentially the same length in the direction of movement of the supporting web as the distance between two adjacent tongues of material.

In order to make it possible to attach elastic organs along a part smaller than half the length of an edge of an absorbing article, sections of the protruding tongues of material may be removed when the laminate is divided.

It is furthermore possible to divide the laminate in such a way that one part of the web has tongues of material which are shorter in the direction of movement of the supporting web than the tongues of material which have been formed on the other part of the web. When attaching the two parts of the web along opposite edges of an absorbing article different elastic properties can thus be obtained along the two edges.

The invention further comprises an elastic laminate which is characterized in that the supporting layer has the shape of a moving supporting web with a wave-shaped, or pointy, edge, whereby the supporting web has tongues of material formed by the supporting layer which protrude from a strip-shaped section of the supporting web, and in that elastic pieces of material have been attached in a pretensioned state to the protruding tongues of material.

In one embodiment, the distance between two adjacent tongues of material is essentially the same as the length of a tongue of material in the direction of movement of the supporting web.

In another embodiment, the distance between two adjacent tongues of material is greater than the length of a tongue of material in the direction of movement of the supporting web.

The pieces of elastic material may consist of strip-shaped sections of an elastic material. Alternatively the pieces of elastic material may be formed by a plurality of parallel elastic strips or threads.

An absorbing article according to the invention is characterized in that it comprises an elastic laminate which has a strip-formed section of supporting material, and at least one tongue of elastic material joined to the section of supporting material, wherein the tongue of material comprises a layer of supporting material and a layer of elastic material, and whereby at least the strip-shaped section of supporting material is firmly attached to the cover of the article.

The absorbing article usually has two longitudinal side-edges, two transverse end-edges and two opposed surfaces, with the strip-shaped section of supporting material arranged along at least one edge of the article and attached to one of the opposing surfaces of the article.

In one embodiment, the laminate is folded around the edge of the article and the tongue of elastic material is attached to the other of the opposing surfaces of the article.

According to another embodiment, the strip-shaped section of supporting material is attached along at least one of the side-edges of the article, with the tongue of elastic material protruding from the side-edge and forming a side-flap on the article, which side-flap has such form and size that it may be folded around a leg-edge of a pair of underpants and is preferably provided with means for fastening of the flap to the underpants.

Preferably, at least two elastic laminates are attached to the cover of the article, For reasons of production, it is in this context suitable if the elastic laminates are attached along two opposed edges of the article.

Since the severed pieces of the elastic elements in the split laminate are fixedly attached to a strip-shaped support material, it is possible to handle and attach the elastic organs with high precision in a continuous process even at high speeds of manufacturing. Since the supporting material is relatively non-elastic, it is possible to control both the distances between the respective pieces of elastic elements and their position with respect to a product web onto which the elastic laminate is applied.

Which material to use as supporting material depends on how the cut material is to be attached to an absorbing article and which function it is expected to have in the finished article. Suitable supporting materials in this context are different types of woven or non-woven textile materials so-called non-woven materials, nets, foam layers, or perforated or non-perforated plastic film. It is furthermore possible to use laminates of some or more layers of any or several of the above mentioned types of materials as supporting material. It is essential for the invention that the supporting material is relatively non-elastic, at least in the direction of movement of the production web.

BRIEF DESCRIPTION OF THE DRAWINGS

The invention will be described in the following in greater detail, with reference to the embodiments which are shown in the attached drawings.

Figure 1:
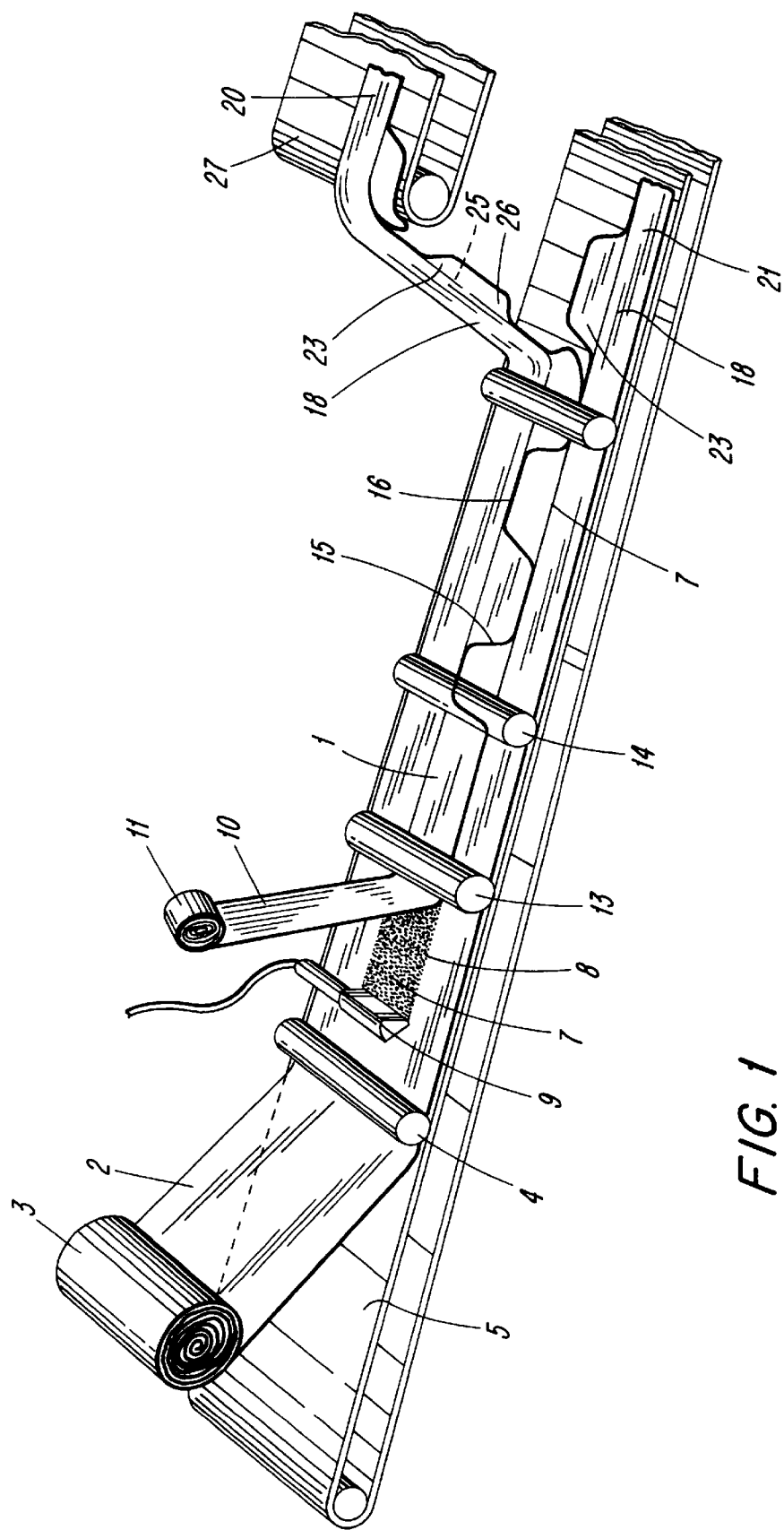
Figure 2:
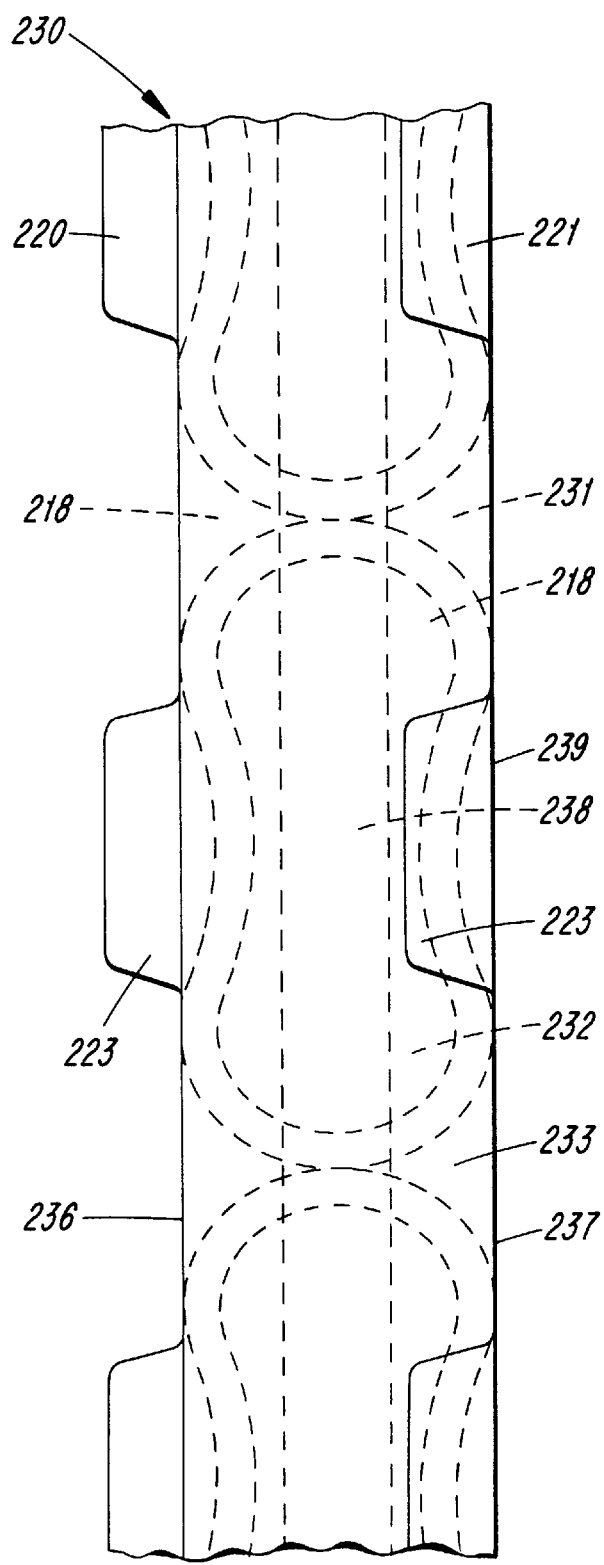
Figure 3:
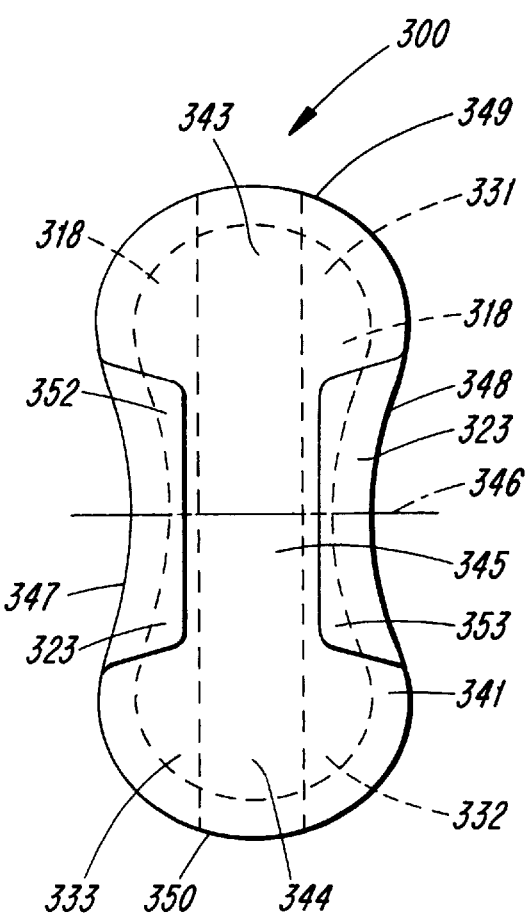
Figure 4:
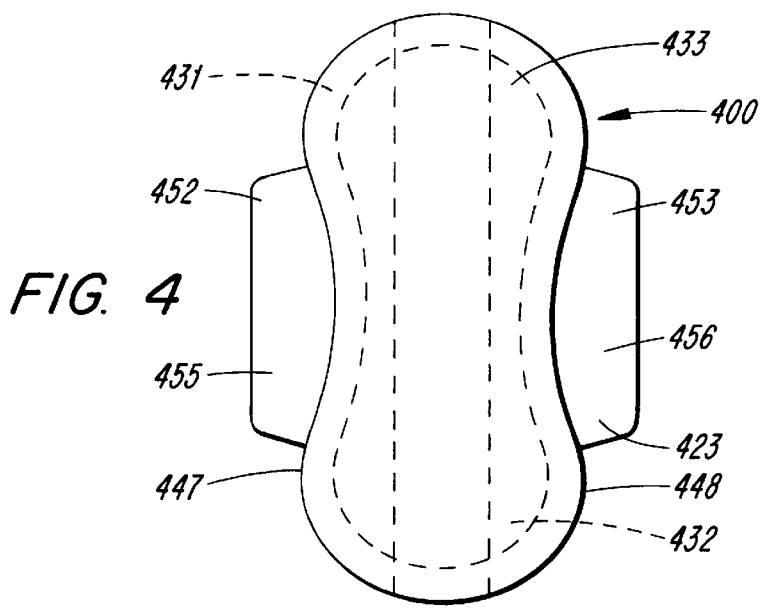
Figure 5:
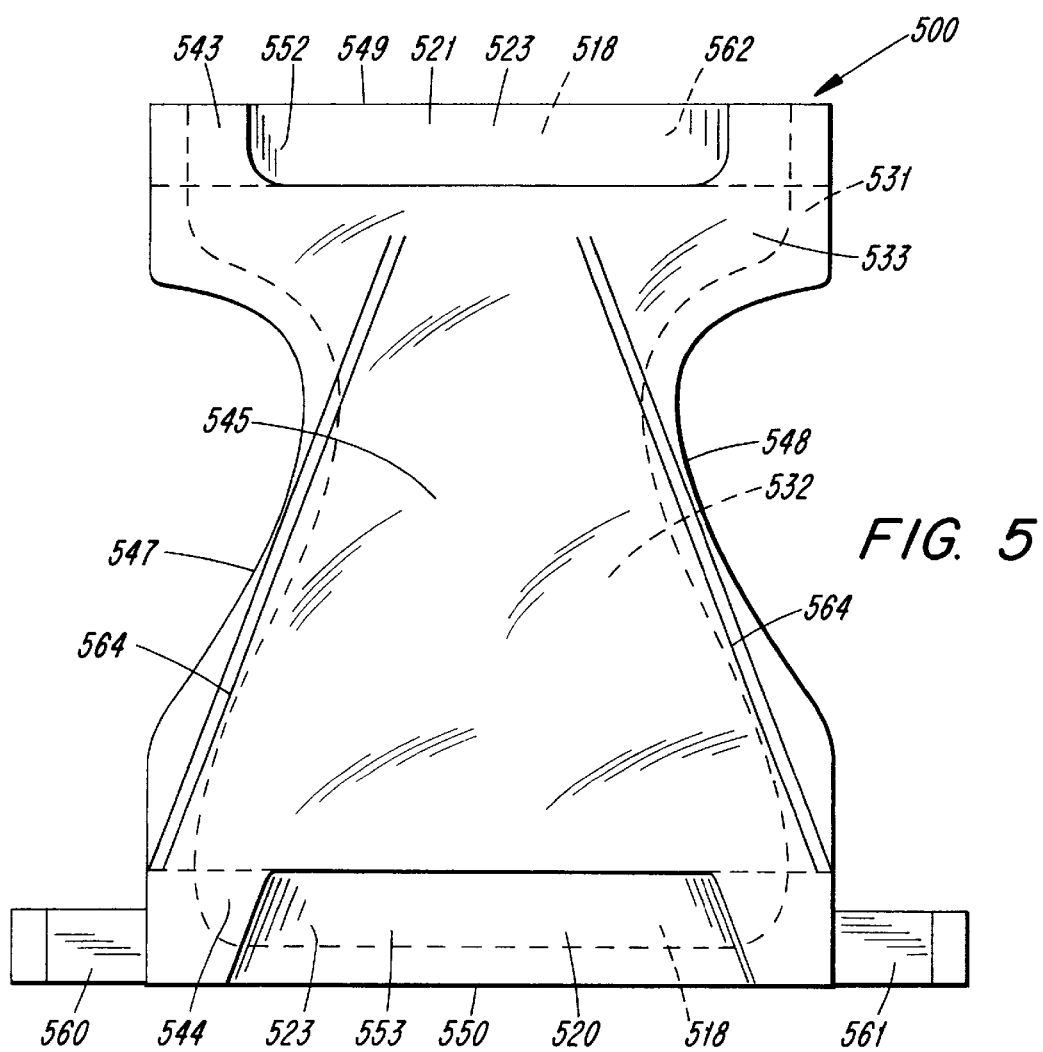
Figure 6:
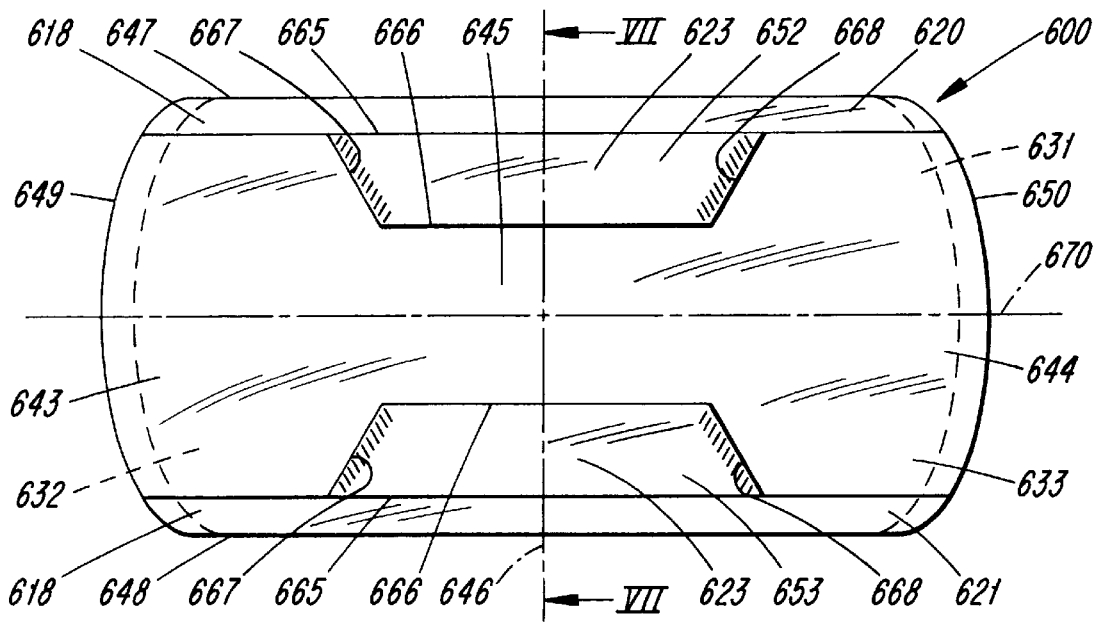
Figure 7:
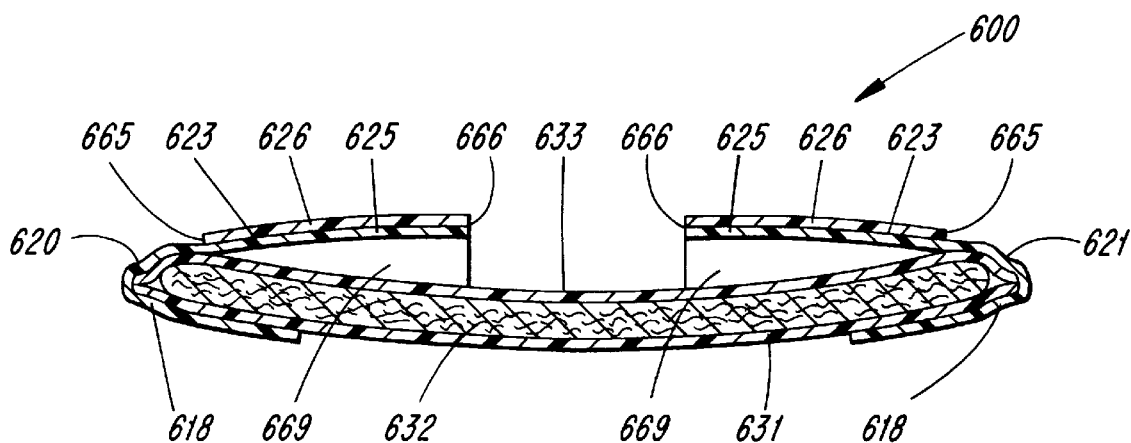
Figure 8:
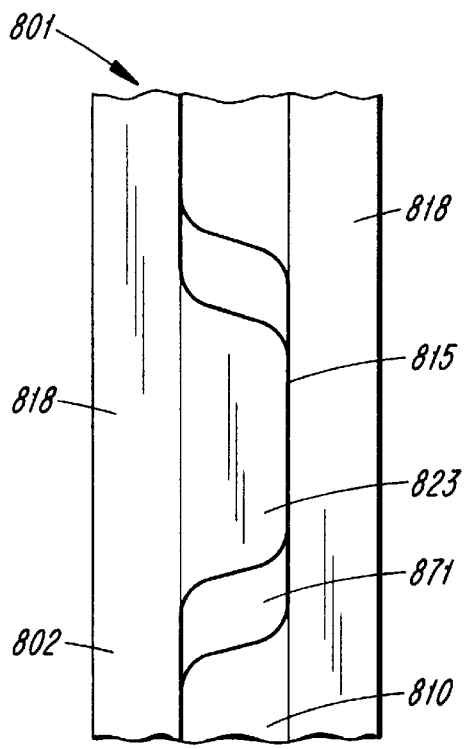
Figure 9:
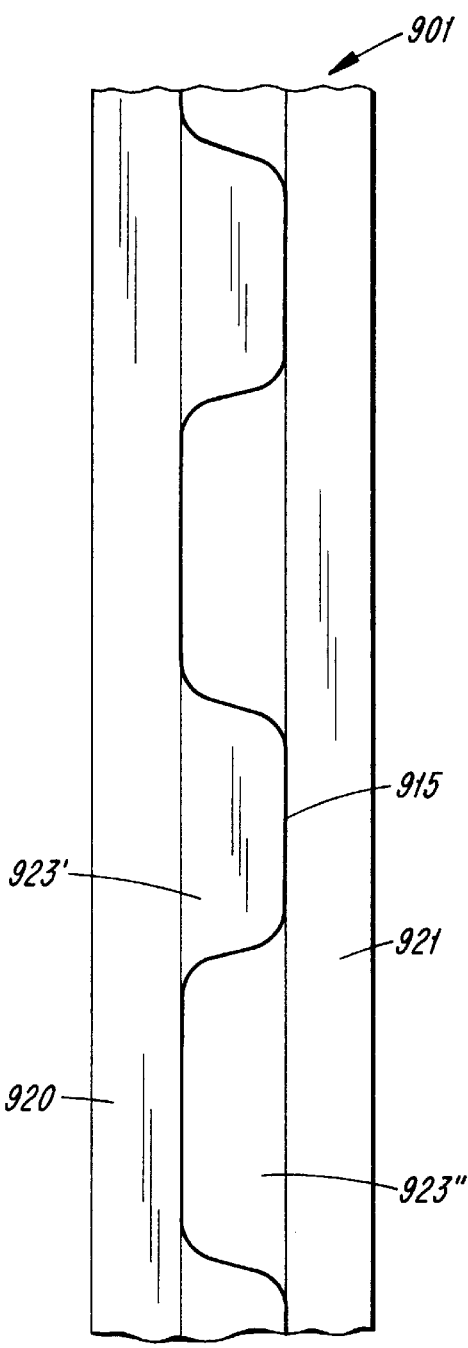
Figure 10:
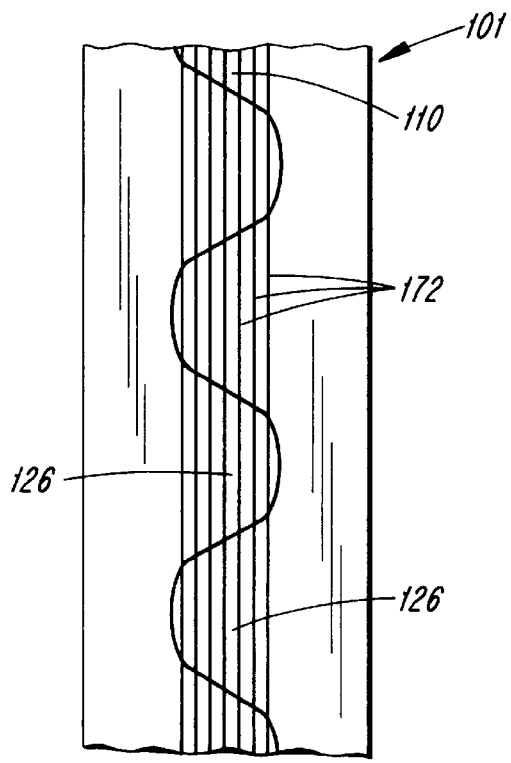

Brief description of the drawings:

FIG. 1 shows schematically how an elastic element is laminated together with a supporting layer after which the laminate is cut in two in the longitudinal direction;

FIG. 2 shows a piece of a continuous web of material out of which separate incontinence protectors can be cut;

FIG. 3 shows an incontinence protector with elastic element according to the invention;

FIG. 4 shows a sanitary napkin with elastic side-flaps;

FIG. 5 shows a diaper with elastic elements attached to the waist-edges;

FIG. 6 shows an incontinence protector according to a further embodiment;

FIG. 7 shows a cross-section through the incontinence protector of FIG. 6 taken along the line VII—VII of FIG. 6;

FIG. 8 shows an alternative dividing pattern for an elastic laminate;

FIG. 9 shows yet another dividing pattern for an elastic laminate;

FIG. 10 shows an elastic laminate with an elastic organ consisting of a plurality of elongated elastic strips or threads.

DESCRIPTION OF EMBODIMENTS

In the production process for an elastic laminate 1, shown in FIG. 1, a first web 2 of supporting material is fed from a first supply roll 3 and, via a first cylinder 4, is positioned on a moving conveyor belt 5. The supporting web 2 consists of a thin layer material with sufficient tensile strength to resist the tensile forces which occur during the manufacturing process without tearing. Suitable materials are, for example, non-woven layers, plastic films, nets, etc. The term non-woven is here taken to mean non-woven textile materials which have been bonded to form coherent fibrous webs by, for example, calandering, ultrasonic bonding, mechanical entanglement with high-pressure water jets, needling, etc, or by activating a special adhesive component in the material. The material which is to be used in the supporting web 2 is determined by the end use of the elastic laminate 1.

A central section 7 of the supporting web 2 which extends in the direction of movement of the conveyor belt is coated with a thin layer of melted glue 8 which is fed from a glue nozzle 9.

A web of elastic material is fed from a second supply roll 11 and positioned on top of the supporting web 2 of the conveyor belt 5. The speed with which the elastic web 10 is fed is lower than the speed with which the supporting web 2 is fed which causes the elastic web 10 to be stretched before it is positioned on the supporting web 2. The elastic web 10 is thinner than the supporting web 2 and has the same width as the glue-coated central section 7 of the supporting web 2. The elastic web 10 is laminated to with the supporting web 2 by being pressed against the glue-covered section 7 of the supporting web 2 by a second cylinder 13. Preferably the elastic web 10 is symmetrically positioned along the central section 7 of the supporting web 2 as shown in FIG. 1, so that the longitudinal centre-lines of the two webs of material coincide. It is, however, also possible to position the webs of material asymmetrically with respect to each other, if this is found to be suitable for the further use of the finished elastic laminate.

The way in which the two webs of material 2, 10 are laminated is of course not significant to the invention. It is thus possible to use other methods of lamination, such as welding with heat or ultrasonically, spray-gluing or gluing with other kinds of adhesive and/or coating patterns.

The webs of material 2, 10 which have been joined together to form a laminate 1 are thereafter made to pass a cutting roll 14 which serves the laminate 1 in the longitudinal direction, i.e. in the direction of movement of the conveyor belt 5, along an undulating dividing line 15 which runs back and forth across the entire width of the elastic web 10. The dividing line 15 runs along one side-edge 16 of the elastic web 10, somewhat outside of the side-edge 16, after which it crosses the web 10 and runs along a section of its other side-edge 17, outside of the side-edge 17, after which the dividing line 15 again crosses the elastic web 10.

By being cut apart, the elastic web 10 is divided across the longitudinal direction of the laminate 1, while continuous strip-shaped sections 18 of the supporting web 2 remain on both sides of the divided elastic web 10. After the cutting step the laminate 1 thus forms two symmetrical halves 20,21 which both have a strip-shaped supporting section 18 with attached tongues 23 of material. The tongues 23 of material are formed when severing the laminate 1 and each tongue 23 of material comprises a flap 25 of the material of the supporting web 2 and an elastic piece of material 26.

After the cutting step, one web-half 20 is preferably led via a transport means 27 a longer distance than the other half of the web 21, by which procedure the two web-halves 20,21 can be displaced with respect to each other in the longitudinal direction so that the position of the protruding tongues of material 23 from the strip-shaped sections 18 of the supporting web 2 can be synchronized with respect to each other. Such synchronization is for example suitable when the two web-halves 20,21 are to be attached along the side-edges of an absorbing article and are to be positioned exactly opposite each other.

It is of course also possible to roll the two-halves 20,21 onto supply rolls which can be used independently of each other in subsequent production stages.

The product web 230 shown in FIG. 2 consist of a continuous laminate of material out of which separate absorbing articles such as incontinence protectors or sanitary napkins can be punched, cut out or severed. The product web 230 comprises a covering layer 231 of liquid impermeable material attached to the side of the web 230 facing away from the viewer. Hourglass-shaped absorption bodies 232 are attached one after another in the longitudinal direction of the liquid impermeable covering layer 231. The absorption bodies 232 are placed with their longitudinal direction corresponding to the longitudinal direction of the product web 230. A liquid permeable covering layer 233 is positioned over the absorption bodies 232 so that the absorbtion bodies 232 are enclosed between the liquid impermeable covering layer 231 and the liquid permeable covering layer 233. The two covering layers 231, 233 are attached to each other, for example by means of gluing, or welding with heat or ultrasonically, along the perimeter of the absorbtion bodies 232.

An elastic laminate of the kind shown in FIG. 1, severed along an undulating dividing line, comprising a web of elastic material 10 and a supporting web 2, is applied with one half 220,221 of the laminate along each side-edge 236,237 of the product web 230. The laminate parts 220,221 are joined to the product web 230 with the strip-shaped, continuous section 218 attached to the liquid impermeable covering layer 231 along both side-edges 236,237 of the product web 230.

After attaching the strip-shaped sections 218 to the liquid impermeable covering layer 231, the attached elastic tongues of material 233 can be folded in over the liquid permeable covering layer 233 of the product web 230 and be attached to this by gluing, or in some other conventional manner. FIG. 2 shows the product web 230 with the elastic tongues 223 of material folded in along a straight folding line 239 along one of the side-edges 237 of the web 230, while the elastic tongues 223 of material along the other side-edge 236 have not been folded in, but protrude from the side-edge 236. In reality, the elastic tongues 223 of material are of course folded on both sides of the product web 230 in over the liquid permeable covering layer 233 in one and the same step of production, if such folding is desirable.

The laminate-halves 220,221 are arranged along the side-edges 236,237 of the product web 230 in such a way that the elastic tongues 223 of material are positioned exactly opposite each other at the narrowest section 238 of the absorption bodies 232.

The incontinence protector 300 shown in FIG. 3 has been cut from the product web 230 shown in FIG. 2. The incontinence protector 300 thus comprises an absorption body 332 enclosed between two covering layers 331,333. The first covering layer 331 is liquid impermeable and is thus intended, during use, to face away from the user and thereby serve as a barrier against fluid leakage from the absorption body 332 out through the covering layer 331. Suitable materials for the liquid barrier are plastic films or layers of non-woven, or paper which has been treated, for example, by being covered with a liquid resistant material in order to achieve impermeability to liquid. The liquid impermeable covering layer 331 can preferably consist of a material which permits the passage of water-vapour and air through the layer.

The second covering layer 333 is liquid permeable and is intended, during use, to receive and admit body fluids to the absorbtion body 332 inside of it. Materials suitable for use as liquid permeable covering layer 333, are for example non-woven, perforated plastic films, nets and various kinds of liquid permeable laminates. The liquid permeable covering layer 333 should be soft and have a skin-friendly surface on that side of the layer 333 which faces the user.

A margin-section 341 of each of the two covering layers 331,333 protrudes somewhat outside of the edges 332 of the absorption body along its entire perimeter. The two protruding margin sections 341 are attached to each other around the absorption body 332. The attachment can be done with any binding means used within this field of technology and the purpose of it is to enclose the absorbtion body 332 between the covering layers 331,333.

The incontinence protector 300 has an elongated hour-glass shape and two wider end-portions 343,344, and a narrower immediate crotch-portion 345. The crotch-portion 345 is the part of the incontinence protector 300 which, during use, is intended to be positioned in the crotch of the user between the users thighs and is furthermore the part of the incontinence protector 300 which will first be struck by secreted body fluids. The length of the crotch-portion 345 and its position in the longitudinal direction of the incontinence protector 300 can vary somewhat during use depending on the anatomy of the user, the position of the protector in the underwear and the position of the user's body. For reasons of simplicity it can, however, schematically be assumed that a symmetrically-shaped incontinence protector 300, such as that shown in FIG. 3, has a crotch-portion 345 which comprises essentially half the length of the incontinence protector 300 and is symmetrically positioned with respect to a transverse centre-line 346 through the protector 300.

The incontinence protector 300 furthermore has two inwardly curved longitudinal side-edges 347,348, and two outwardly curved transverse end-edges 349,350.

Elastic elements 352,353 are attached in a pretensioned state along the longitudinal side-edges 347,348 at the crotch-portion 345 of the incontinence protector. The elastic elements 352,353 consist of a laminate of the kind shown in FIG. 1 and thus consist of a supporting layer 2 and an elastic layer of material 10. The elastic elements 352,353 are attached across essentially their entire surface to the liquid permeable covering layer 333 at the side-edges 347,348 of the incontinence protector. The strip-shaped sections 318 which after the manufacturing of the elastic laminate are joined to the elastic elements 352,353 are attached to the liquid impermeable covering layer 331 along the longitudinal side-edges 347,348 of the entire incontinence protector.

Since the side-edges 347,348 of the incontinence protector curve inwards from the straight folding line 239 formed in the elastic laminate 301, folding around the side-edges 236,237 of the continuous product web 230 as shown in FIG. 2, the connection between the elastic elements 352,353 and the strip-shaped sections 318 is cut off simultaneously with cutting the incontinence protector 300 from the product web 230. In the finished incontinence protector 300 the strip-shaped parts 318 thus form separate components arranged on the liquid impermeable covering layer 331 and are completely severed from the elastic organs 352,353.

By choosing a suitable material as supporting layer, it is possible to achieve advantages in the form of increased user comfort. It can for example be suitable to make the supporting layer from a soft non-woven layer which creates a comfortable textile surface, on the outside of the liquid impermeable covering layer 331 along the side-edges 347, 348. Since these parts of the liquid impermeable covering layer 331 are often bent into the groin of the user during use, they will thereby come into direct contact with the skin of the user. By providing a soft textile material on the outside of the liquid impermeable covering layer 331 along the side-edges 347,348, the risk of abrasion and irritation of the skin is considerably reduced. Furthermore, the comfort for the user increases since the risk that the incontinence protector is perceived as sweaty, or that it sticks to the skin, is small.

An incontinence protector 300 of the kind shown in FIG. 3 is intended to be worn inside a pair of underpants and to be detachably attached inside the underwear. The attachment is done by means of special attachment elements, usually in the form of surfaces of pressure sensitive self-adhesive glue arranged on the liquid impermeable covering layer 331. Other kinds of attachment means, such as hook-and-loop, push-buttons, friction coatings, and combinations of these, may occur. The attachment element is not shown in the drawings.

FIG. 4 shows a sanitary napkin 400 of the same principal shape and construction as the incontinence protector 300 of FIG. 3. The sanitary napkin shown in FIG. 4 is also cut or punched out from a product web 230 of the kind shown in FIG. 2. The sanitary napkin 400, however, differs from the incontinence protector 300 in that the elastic elements 452,453 have not been folded in over and attached to the liquid impermeable covering layer 433, but form protruding side-flaps 455,456 at the side-edges 447,448 of the sanitary napkin.

During use of the sanitary napkin, it is usually attached inside a pair of underpants, preferably by means of an attachment element (not shown) on the liquid impermeable covering layer 431. The protruding elastic side-flaps 455, 456 are folded around the leg-edges of the underwear and are attached on the outside of the crotch-section of the underwear, preferably using self-adhesive glue, hook-and-loop, etc, arranged on the surface of the side-flaps 455,456 which faces the underpants. The attachment elements of the side-flaps are not shown in the drawings either.

Since the side-flaps 455,456 consist of an elastic material, it is easy to fold them around the leg-edges of the underwear. The elastic material conforms to the contour of the leg-edges, without causing sharp wrinkles or folds which might be unpleasant for the user.

At the same time as the elastic side-flaps 455,456 serve as leakage protection for the underwear and contribute to keeping the sanitary napkin 400 in place during use they also serve as conventional elastic elements 452,453. Since the web of elastic material during the manufacturing of an elastic laminate according to the invention is attached to the supporting web in a stretched condition, the side-flaps 455,456 strive to contract when the tension ceases. In so doing they give the entire sanitary napkin a bent shape in the longitudinal direction. The elastic side-flaps 455,456 mainly affect only the side-edges 447,448 of the sanitary napkin so that these contract. The material in the absorbtion body 432 between the side-edges 447,448 is however relatively stiff and difficult to contract. This causes the absorbtion body 432 between the elastic side-flaps 455,456 to curve outwards from the plane of the sanitary napkin. It is possible to control the direction of curving by manipulating the sanitary napkin.

When heavy flows of liquid are expected, it is usually suitable if the absorption body 432 curves outwards, in the direction of the liquid impermeable covering layer 431. In this way, a fluid receiving bowl is shaped on that side of the sanitary napkin which, during use, is intended to face the user. If, however, the anticipated flow of fluid is smaller and the sanitary napkin can be expected to have the ability to immediately absorb all the secreted body fluid, it may instead be suitable if the absorption body 432 is bent in the direction of the liquid permeable covering layer 433. This is due to the fact that in so doing, a soft hump is formed which, during use, can be in direct contact with the body and absorb all body fluids as soon as they are secreted from the body. The user may by pressing the absorption body 432 in one or the other direction, in a simple manner control the bending in the desired direction. The shape that the sanitary napkin 400 is given may of course also be chosen by the user according to the way she feels to be the most functional and comfortable.

FIG. 5 shows a diaper of the so-called all-in-one type. The diaper 500 has the same principal construction as the incontinence protector 300 and the sanitary napkin 400 of FIGS. 3 and 4. Thus the diaper comprises an absorption body 532 enclosed between a liquid impermeable covering layer 531 and a liquid permeable covering layer 533.

The diaper 500 is essentially T-shaped. The transverse section of the T forms the forward portion 543 of the diaper which is intended, during use, to be positioned in front of the user and across the belly of the user. The leg of the T is widened towards the rear portion 544 of the diaper, which is that portion which, during use, is intended to be positioned towards the rear of the user and be arranged over the user's seat. Between the forward portion 543 and the rear portion 544, the diaper has a narrower crotch-portion 545 which, during use, is intended to be positioned in the crotch of the user. The diaper further has two longitudinal side-edges 547,548 shaped with inwardly curved sections which, during use, form leg-edges which enclose the thighs of the user, and two transverse straight end-edges 549,550 which, during use, together make up the waist-edge of the diaper.

During use the diaper 500 is intended to be fastened so that it in a pant-like fashion encloses the lower portion of the users torso, and to this end it is provided with self-adhesive tape-tabs 560,561. The tape-tabs 560,561 are arranged at both side-edges 547,548 of the rear portion 544 of the diaper, close to the rear end-edge 550. The fastening of the diaper is made by bringing the tape-tabs 560,561 to adhere to the outside of the forward portion 543 of the diaper, close to the forward end-edge 549. The part of the forward portion 543 which is intended to be the attachment area 562 for the tape-tabs 560,561 is provided with a reinforcement layer 518 in the form of a layer of plastic film which permits detachable attachment of the tape-flaps 560,561. By reinforcing the liquid impermeable covering layer 531 it is possible to open and reclose the diaper 500 without tearing or ripping the liquid impermeable covering layer 531.

Other kinds of fastening means such as hook-and-loop, safety pins, clips, push-buttons, etc can of course be used for fastening the diaper.

The diaper of FIG. 5 further has elastic elements in the shape of double elastic threads 564 arranged along two lines which extend from the forward portion 543 of the diaper to its rear portion 544. The lines diverge in the direction of the rear portion of the diaper so that the elastic threads 564 form a V-shaped pattern with its apex towards the forward edge 549 of the diaper. When the diaper is worn, the elastic threads 564 provide an elastic closing of the diaper around the thighs of the user. The position of the elastic threads 564 also contributes to shaping the diaper, both in the longitudinal and in the transverse directions, so that its shape is adapted to the shape of the users body.

Two further elastic elements 552,553 are arranged along both the forward 549 and the rear end-edge 550. The elastic elements 552,553 are made up of halves 520,521 of an elastic laminate in accordance with the invention. Both halves of elastic laminate 520,521 thus consist of a supporting layer in the form of a plastic film which has a strip-shaped section 518 and a tongue 523 of material attached to this, which consists of a protruding flap 525 of supporting material which has been laminated together with an elastic piece of material 526 and which tongue 523 of material forms the elastic element 552,553.

The elastic elements 552,553 are attached along the end-edges 549,550 of the diaper by gluing, or in some other way attaching the strip-shaped section 518 to the outside of the liquid impermeable covering layer 531. The elastic tongue 523 of material with protrudes from the strip-shaped section 518 is subsequently folded around the respective end-edges of the diaper 549,550, after which the tongue 523 of elastic material is attached to the liquid permeable covering layer 533. To avoid the elastic material during use coming into direct contact with the skin of the user, it may be suitable to arrange a layer of, for example, soft non-woven material over the elastic element 552,553 on that side of it which is intended to face the user. Alternatively, the elastic element 552,553 can be formed of an elastic material which in itself is soft and pleasant for the skin, for example elastic non-woven materials, woven elastic materials, core-spun elastic threads, elastic foam strips, etc.

The strip-shaped section 518 which is arranged on the outside of the diaper constitutes the reinforced attachment area 562 at the forward section 543 of the diaper for attaching the tape-flaps 560,561 which has been mentioned above.

FIGS. 6 and 7 show yet another incontinence protector 600 provided with elastic elements 652,653 in accordance with the invention. As with the above described absorbing articles, the incontinence protector 600 comprises an absorption body 632 enclosed between a liquid impermeable covering layer 631 and a liquid permeable covering layer 633.

The incontinence protector 600 has an essentially rectangular shape with straight longitudinal side-edges 647,648, whereas the end-edges 649,650 are rounded outwardly. The incontinence protector 600 further has two end-portions 643,644 and an intermediate crotch-portion 645. The crotch-portion 645 constitutes approximately half the length of the incontinence protector 600 and is symmetrically positioned with respect to a lateral centre-line 646 through the incontinence protector.

Along the side-edges 647,648 of the incontinence protector, there are sections 620,621 of an elastic laminate cut into two, according to the invention. The laminate sections 620,621 consist of a strip-shaped section 618 of supporting material and a tongue 623 of material comprising a flap 625 which protrudes from the strip-shaped section 618, and an elastic piece of material 626 laminated to the supporting flap 625. Both of the elastic laminate parts 620,621 are attached with an external section of the strip-shaped section 618 on the outside of the liquid impermeable covering layer 618 on the outside of the liquid impermeable covering layer 631 along both side-edges 647,648 of the incontinence protector. An inner part of the strip-shaped section 618 is this together with the tongues 623 of elastic material, subsequently folded around the respective side-edges 647,648 and is attached to the outside of the liquid permeable covering layer 633.

The sections 626 of elastic material are, in a non-stretched state, of an elongated mainly rectangular shape with two longitudinal edges 665,666 and two lateral edges 667,668. Since each section 626 of elastic material is attached to the strip-shaped section 618 along a first longitudinal edge 665, the piece 626 of elastic material is kept stretched along the first edge 665 during the manufacturing process. The other longitudingal edge 666 can however contract somewhat in the direction of the piece 626 of elastic material, whereby the piece 626 of elastic material assumes the shape shown in FIG. 6. As can be seen in FIG. 6, the transverse edges 667,668 of the piece 626 of elastic material are oblique and converge in towards the lateral centre-line 646 of the incontinence protector.

The tongues 623 of elastic material are attached to the outside of the liquid permeable covering layer 631 only along the oblique transverse edges 667,668. The tongues 623 of material can be attached by, for example, gluing or welding with heat or ultrasonically. Since the tongues 623 of material are attached only along their oblique transverse edges 667,668, pockets 669 are formed between the tongues 623 of material and the liquid permeable covering layer 633. The pockets 669 are open inwardly towards the longitudinal centre-line 670 of the incontinence protector. Since the tongues 623 of elastic material contract when the stretching of the incontinence protector ceases after manufacturing, the incontinence protector is bent along the longitudinal centre-line 670. Thereby the tongues 623 of material are lifted up from the liquid permeable covering layer 633 and the pockets 669 are opened, which can best be seen in FIG. 7.

During use of the incontinence protector 600, the pockets 669 serve as fluid reservoirs when large amounts of body fluid rapidly flow across the incontinence protector. The fluid is thus gathered into the pockets 669 and prevented from flowing out over the side-edges 647,648 of the incontinence protector. The material of the pockets 669 is suitably liquid-tight, or such that they at least can resist penetration of fluid during the time necessary for the body fluid to be absorbed into the absorption body 632 of the incontinence protector. It is, however, advantageous if air and water vapour can pass through the material.

As with the earlier described incontinence protector 300 and the sanitary napkin 400, the incontinence protector 600 is preferably equipped with some sort of attachment means for detachable fastening of the protector inside a pair of underpants.

FIG. 8 shows an alternative embodiment of a dividing pattern 815 for the severing of a laminate 801 which consists of a wider supporting web 802 and a narrower, elastic material web 810. When dividing the laminate 801 shown in FIG. 8, small mainly rhomboid-shaped parts 871 of the laminate 801 are cut out between the tongues 823 of material which remain. By cutting out certain sections 871 of the laminate, it is possible to control the length of the tongues 823 of elastic material with respect to the length of the strip-shaped sections 818. In so doing, elastic elements can be attached to an absorbing article along a part smaller than half the extension of the article in the direction of manufacturing. During the earlier described severing of the elastic laminate, the severing curve must be adapted so that the severed elastic tongues of material are of approximately the same length along a moving product web as half the extension of the absorbing articles in the direction of movement of the product web.

The dividing line 915 shown in FIG. 9 will result in the laminate 901 being divided into two web-halves 920,921 of different appearance. One web-half 920 has shorter tongues 923' of material, while the tongues 923" of material on the other web-half 921 are of a greater length. Such a dividing line 915 could for example be useful when manufacturing waist-elastics on diapers if different lengths of the elastic elements at the rear respectively front-edges of the diaper are desired.

FIG. 10 shows an elastic laminate 101 where the elastic material web 110 consists of a plurality of parallel elastic strips or threads 172.

In the described examples the different absorbing articles have been shown in a flat state, i.e. with the elastic elements stretched. This has been done in order to more clearly show the respective positions of the components in the article. In reality, however, the absorbing articles have a three-dimensional curved shape caused by the contraction of the elastic elements which have been attached with a pre-tension.

The embodiments shown should not be considered as limiting the invention; instead, a number of further variants and modifications are possible within the scope of the invention. It is, for example, possible to in an absorbing article to attach the strip-shaped section of the supporting layer on the liquid permeable covering layer of the article and to fold in and attach the tongue of elastic material against the liquid impermeable covering layer of the article.

What is claimed is:

1. A method of manufacturing an elastic laminate in which a web of elastic material, with at least two side edges, is continuously fed, stretched, and attached in stretched condition to a supporting material in the form of a moving supporting web, with at least two side edges, wherein the supporting web has a larger extension across the direction of movement of the supporting web than the web of elastic material, and wherein the web of elastic material is attached to the supporting web with sections of the supporting web protruding laterally on each side of the web of elastic material, after which the laminate of the supporting web and the web of elastic material is divided into two longitudinal web-sections along a curve-shaped dividing line which extends substantially in the direction of movement of the supporting web inside of edges of the supporting web, and curves back and forth across the web of elastic material, whereby tongues of material, formed from pieces of the web of elastic material and flaps of the supporting web which have been laminated together, protrude from and are connected to strip-shaped edge-sections of the supporting web on each side of the dividing line.

2. The method according to claim 1, wherein the web of elastic material and the web of supporting material each comprise a longitudinal centre-line, and a width of each web is the distance between the two side edges of the respective webs, and wherein the dividing line extends mainly along the longitudinal centre-line of the web of elastic material and curves out in both directions from that centre-line with an amplitude corresponding to at least half of the width the web of elastic material.

3. The method according to claim 2, wherein the web of elastic material is attached to the supporting web with the longitudinal centre-line of the web of elastic material substantially coinciding with the longitudinal centre-line of the supporting web.

4. The method according to claim 1, wherein the laminate is divided along the dividing line such that adjacent protruding tongues of material on each web-section are separated by a first distance, and the protruding tongues extend in the direction of movement of the supporting web a second distance, and wherein the first distance is essentially the same as the second distance, whereby the laminate is divided into two symmetrical web-sections.

5. The method according to claim 1, wherein sections of the protruding tongues of material are removed when the laminate is divided.

6. The method according to claim 1, wherein the laminate is divided in such a way that a first web-section has tongues of material which have a smaller extension in the direction of movement of the laminate than those tongues formed on a second web-section.

7. An elastic laminate comprising: a supporting layer and elastic pieces of material connected to the supporting layer, wherein the supporting layer is made up of a supporting web with a first and a second longitudinal side-edge, wherein only one of said first and said second longitudinal side-edges exhibits an undulating shape or pointy shape forming tongues of material formed from the supporting layer and protruding out from a strip-shaped section of the supporting web, and wherein the elastic pieces of material are attached to the protruding tongues of material in a pre-tensioned state.

8. The elastic laminate according to claim 7, wherein protruding tongues of material extend longitudinally a first distance, and adjacent protruding tongues are separated by a second distance, such that the first distance is essentially the same length as the second distance.

9. The elastic laminate according to claim 7, wherein protruding tongues of material extend longitudinally a first distance, and adjacent protruding tongues are separated by a second distance, such that the distance between two adjacent tongues of material is greater than the distance that a tongue of material extends longitudinally.

10. The elastic laminate according to claim 7, wherein the elastic pieces of material are in the form of strip-shaped pieces of elastic material.

11. The elastic laminate according the claim 7, wherein the elastic pieces of material are in the form or two or more parallel elastic strips or threads.

12. An absorbent article comprising an absorption body enclosed in a covering layer, wherein the article comprises an elastic laminate which has a strip-shaped supporting section, which is relatively non-elastic, and at least one elastic tongue of material joined to the supporting section, whereby at least one elastic tongue of material comprises a layer of supporting material and a layer of elastic material, and whereby at least the strip-shaped, relatively non-elastic, supporting section is firmly attached to the covering layer of the article.

13. The absorbing article according to claim 12, wherein the article has two longitudinal side-edges, two transverse end-edges and first and second opposed surfaces in which the strip-shaped supporting section is arranged at least one edge of the article and is attached to the first opposed surface of the article.

14. The absorbing article according to claim 13, wherein the laminate is folded around an edge of the article, along which the strip-shaped supporting section is arranged, and wherein the tongue of elastic material is attached to the second opposed surface of the article.

15. The absorbing article according to claim 13, wherein the strip-shaped supporting section is attached along at least one of the side-edges of the article, and in that the elastic tongue of material protrudes from the side-edge and forms a side-flap on the article, which side-flap is of such shape and size that it can be folded around a leg-edge of a pair of underpants and comprises means for attaching the flap to the underwear.

16. The absorbing article according to claim 12, wherein at least two elastic laminates are attached to the covering layer of the article.

17. The absorbing article according to claim 16, wherein the elastic laminates are attached along two opposed edges of the article.

18. The absorbing article according to claim 12, wherein said article is one of a diaper, incontinence protector, and a sanitary napkin.

* * * * *